United States Patent [19]

Howell et al.

[11] Patent Number: 5,420,037
[45] Date of Patent: May 30, 1995

[54] PROCESS FOR SEPARATION OF ENANTIOMERIC 3-MERCAPTO-2-SUBSTITUTED ALKANOIC ACID USING LIPASE P30 AND SYNTHESIS OF CAPTOPRIL TYPE COMPOUNDS

[75] Inventors: Jeffrey M. Howell, Chatham; Ramesh N. Patel, Bridgewater; Laszlo J. Szarka, East Brunswick, all of N.J.

[73] Assignee: E. R. Squibb & Sons, Inc., Princeton, N.J.

[21] Appl. No.: 180,517

[22] Filed: Jan. 12, 1994

Related U.S. Application Data

[63] Continuation of Ser. No. 915,148, Jul. 17, 1992, abandoned, which is a continuation-in-part of Ser. No. 412,976, Sep. 26, 1989, abandoned.

[51] Int. Cl.⁶ .......................... C12P 41/00; C12P 17/10
[52] U.S. Cl. ...................................... 435/280; 435/876; 435/121
[58] Field of Search .............................. 435/280, 121

[56] References Cited

U.S. PATENT DOCUMENTS

| | | | |
|---|---|---|---|
| 4,105,776 | 8/1978 | Ondetti et al. | 424/274 |
| 4,601,987 | 7/1985 | Klibanov et al. | 435/280 |
| 4,629,701 | 12/1986 | Sakimae et al. | 435/130 |

OTHER PUBLICATIONS

B. Cambou et al., *Biotechnology and Bioengineering*, vol. XXVI, pp. 1449–1454 (1984).

*Primary Examiner*—David M. Naff
*Assistant Examiner*—S. Saucier
*Attorney, Agent, or Firm*—Theodore R. Furman, Jr.; Ellen K. Park

[57] ABSTRACT

S-enantiomers of the formula

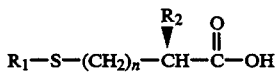

result from the reaction of a racemic form of compound I with an alcohol in the presence of an enzyme capable of selectively esterifying the R-enantiomers of the racemic compound.

4 Claims, No Drawings

PROCESS FOR SEPARATION OF ENANTIOMERIC 3-MERCAPTO-2-SUBSTITUTED ALKANOIC ACID USING LIPASE P30 AND SYNTHESIS OF CAPTOPRIL TYPE COMPOUNDS

This is a continuation of U.S. Ser. No. 07/915,148, filed Jul. 17, 1992, which is a continuation-in-part of U.S. Ser. No. 412,976, filed Sep. 26, 1989 (both now abandoned).

BACKGROUND OF THE INVENTION

Optically active carboxylic acids represented by the formula

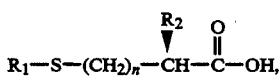   I wherein $R_1$ is hydrogen or

$R_2$ and $R_3$ are each independently selected from alkyl, cycloalkyl, aralkyl or aryl, and n is 1 or 2, are useful, for example, as intermediates for the synthesis of various physiologically active materials. For example, compounds of the formula

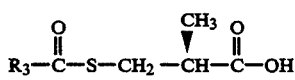   II or

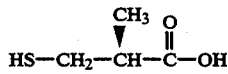   IIa can each serve as a key intermediate in the synthesis of 1-[(2S)-3-mercapto-2-methylpropionyl]-L-proline (captopril), having the formula

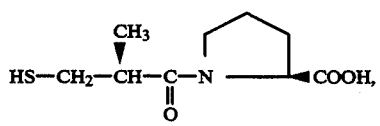   III and [1(R*),2α,4α]-1-[3-(Benzoylthio)-2-methyl-1-oxopropyl]-4-(phenylthio)-L-proline (zofenopril), having the formula

IV

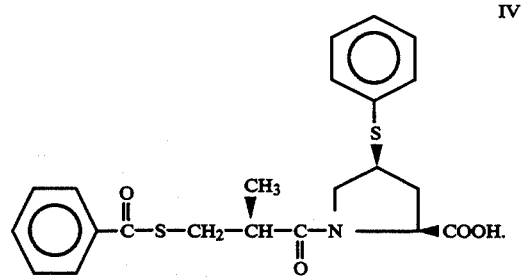

The beneficial activity of captopril and zofenopril depends on the configuration of the mercaptoalkanoyl moiety and the compounds of the S configuration are about 100 times more potent than the corresponding R-enantiomers. Thus, the S-enantiomers illustrated by formula I are much more desirable for these purposes than their R-enantiomer counterparts.

Prior art processes for making captopril and zofenopril have utilized chemical and enzymatic resolution procedures. For example, carboxylic acids of the formula

   I' are prepared as racemic mixtures which can be separated into the R and S-enantiomeric forms using chemical resolving agents. The so-provided S intermediates can then be used to prepare the desired products. The chemical resolution techniques have the distinct disadvantage, however, that large amounts of very expensive resolving agents are required. Additionally, the processes themselves are cumbersome and the yield is relatively low.

Alternatively, racemic compounds of the formula

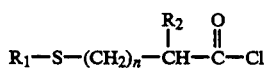   V can be directly coupled to X (which is L-proline in the case of captopril, and L-4-phenylthioproline in the case of zofenopril) to produce diastereomers of the general formula

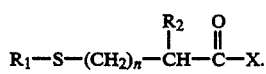   VI

The SS-diastereomer of compound VI can be isolated. Thereafter the sulfhydryl or benzoylthio groups corresponding to captopril and zofenopril, respectively, can be provided to the left side of the molecule by known methods. However, a drawback to this process is that an equal amount of the RS-diastereomer of compound VI is formed which must be discarded. This is highly undesirable in view of the cost of the L-proline and derivatives thereof.

U.S. Pat. No. 4,629,701 provides the desired resolved form of the carboxylic acids of formula I where $R_1$ is acyl by subjecting an ester of the formula

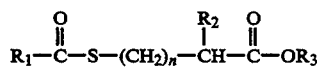   VII to an enzyme capable of asymmetrically hydrolyzing such an ester. It was found that while the

moiety is hydrolyzed to the acid form, the racemic ester is also resolved into the S or R configuration in improved yields and at lower costs than possible with chemical resolution techniques. However, there is still a considerable expense in making these ester starting materials and higher optical purity is still desired for more active products. Therefore, a process which is less expensive with improved yields and which provides enhanced optical purity would be a useful addition to the art.

SUMMARY OF THE INVENTION

In accordance with the present invention a novel process for preparing S-enantiomers having the formula

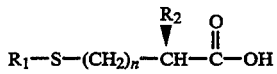

where $R_1$ is hydrogen or

$R_2$ and $R_3$ are each independently selected from alkyl, cycloalkyl aralkyl or aryl; and n is 1 or 2, is provided. The present process comprises reacting a racemic mixture of a compound having the formula

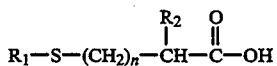

with a compound of the formula

      VIII wherein $R_4$ is alkyl, cycloalkyl, aryl or aralkyl, in the presence of an enzyme or microorganism capable of catalyzing the selective esterification of compounds of formula I' to provide a solution containing R-enantiomeric esters and S-enantiomeric unreacted acids of formula I; and, recovering the resulting non-esterified S-enantiomers of formula I.

DETAILED DESCRIPTION OF THE INVENTION

The following definitions apply throughout this application.

The term "alkyl" as used herein refers to straight or branched chain carbon groups of 1 to 25 carbon atoms, preferably 1 to 6 carbon atoms.

The term "cycloalkyl" as used herein refers to groups containing 5 to 7 carbon atoms.

The term "aryl" as used herein refers to monocyclic or bicyclic aromatic groups containing from 6 to 10 carbon atoms in the ring portion such as phenyl, naphthyl, and substituted phenyl or naphthyl containing substituents such as nitro, halogen, methyl or alkoxy groups on the aromatic ring.

In accordance with the present invention, it has been found that alcohols of formula VIII, in the presence of catalyzing lipases or esterases (or microorganisms producing same), are capable of catalyzing the stereoselective esterification of racemic compounds of formula I'. This process produces esters in the R-enantiomeric form having the formula

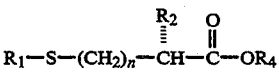

and the resulting "by-product" is in fact, a high yield of optically pure unreacted S-enantiomers of formula I.

The enzymatic resolution process of the present invention has the advantage that it can provide the desired S-enantiomers of formula I with high optical purity and at good yields. Additionally, because the present process uses a racemic carboxylic acid of formula I' as a starting material, instead of the carboxylic acid esters employed in prior art enzymatic processes, there is considerably less expense involved. These and other features make the process of the present invention very attractive for use in preparing optically active compounds of formula I, such as the S-enantiomers of the formula

and

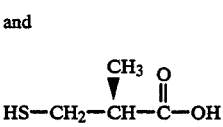

useful in the preparation of captopril and zofenopril.

Methods for obtaining the racemic starting material of the formula

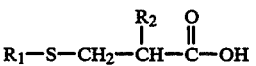

are known.

For example, a compound of the formula

      VII can be coupled to a compound of the formula

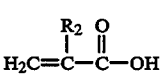

in the presence or absence of a suitable solvent, such as hexane, heptane or isopropanol, under the usual conditions for conducting such an addition reaction.

Compounds of formula

      VIII for use in the present process can be any alcohol suitable for esterifying compounds of formula I'. For example, in a preferred embodiment for providing resolved S-enantiomers of formula II and IIa, methanol, benzyl alcohol and 1-octanol each provided optical purities in excess of 95% at reaction yields of between about 30% and 40%.

The present process can be carried out in an organic solvent. Typical solvents suitable for use in the present process include, but are not limited to, 1,1,2-trichloro-1,2,2-trifluoroethane, toluene, cyclohexane, benzene, hexane, heptane, isooctane and octane.

The enzyme or microorganism used in the present process can be any enzyme or microorganism having the ability to catalyze the stereoselective esterification of acids of formula I'. Various enzymes, such as esterases and lipases, regardless of origin or purity, are suitable for use in the present invention. The enzyme can be in the form of a mixture of animal and plant enzyme, cells of microorganisms, crushed cells or extracts of cells.

Typical genuses of microorganism suitable as sources of catalyzing enzymes include Mucor, Escherichia, Staphylococcus, Agrobacterium, Rhizopus, Aspergillus, Nocardia, Streptomyces, Trichoderma, Candida, Rhodotorula, Torulopsis, Bacillus, Alcaligenes, Pseudomonas, Brevebacterium, Enterobacter, Chromobacterium, Arthrobacter, Microbacterium, Mycohacterium, Saccharomyces, Penicillium, Botrytis, Chaetomium, Ophiobolus, Cladosporium and the like.

Commercially available enzymes suitable for use in the present invention include lipases, such as Amano P (*Pseudomonas fluorescens*) which is preferred, Amano AY-30 (*Candida cylindracea*), Amano N (*Rhizopus niveus*), Amano R (Penicillium sp.), Amano FAP (*Rhizopus oryzae*), Amano AP-12 (*Aspergillus niger*), Amano MAP (*Mucor meihei*), Amano GC-4 (*Geotrichum candidum*), Sigma L-0382 (porcine pancreas), Sigma L-3001 (Wheat germ), Sigma L-1754 (*Candida cylindracea*), Sigma L-0763 (*Chromobacterium viscosum*) and Amano K-30 (*Aspergillus niger*). Additionally, enzymes derived from animal tissue include esterase from pig liver, α-chymotrypsin and pancreatin from pancreas.

Specific microorganisms suitable for use in the present process include *Pseudomonas fluorescens, Pseudomonas putida, Pseudomonas ovalis, Escherichia coli, Staphylococcus aureus, Alcaligenes faecalis, Streptomyces griseus, Streptomyces clavuligerus, Nocardia erthropolis, Nocardia asteraides, Mycobacterium phlei, Agrobacterium radiobacter, Aspergillus niger, Rhizopus oryzae* and the like.

To carry out the process of the present invention, the alcohol of formula VIII and racemic starting material of formula I' are added to the desired organic solvent. The enzyme (or microorganism containing same) is added thereto. Typically, the enzyme is adsorbed onto a suitable carrier, e.g. diatomaceous earth (porous Celite Hyflo Supercel), microporous polypropylene (Enka Accurel ® polypropylene powder), or a nonionic polymeric adsorbent such as Amberlite ® XAD-2 (polystyrene) or XAD-7 (polyacrylate) from Rohm and Haas Co. This serves the purpose of immobilizing the enzyme which has the effects of controlling the enzyme particle size and preventing aggregation of the enzyme particles when used in an organic solvent. This can be accomplished, for example, by precipitating an aqueous solution of the enzyme with cold acetone in the presence of the Celite Hyflo Supercel followed by vacuum drying, or in case of nonionic polymeric adsorbent, incubating enzyme solutions with adsorbent on a shaker for desired time, removing excess solution and drying enzyme-adsorbent resins under vacuum. The reaction solution typically contains between about 5 and 250 mg of racemic starting material per ml of solvent. The enzyme added to the reaction solution may be present in concentrations ranging from about 5 to about 200 mg of enzyme per ml of solvent. While it is desirable to use the least amount of enzyme possible, the amount of enzyme required will vary depending upon the specific activity of the enzyme used.

When the reaction is conducted in an organic solvent, small amounts of water may be added to the reaction mixture. The water added to the reaction mixture may be present in concentrations ranging from about 0.2 to about 100 mg of water per ml of solvent, or solvent saturated with water, and preferably is present in an amount of about 0.5–5 mg/ml. incubation of the reaction solution can be at a temperature between about 4° and about 60° C. and is preferably carried out at about 30°–50° C. The reaction time can be appropriately varied depending upon the amount of enzyme used and its specific activity. Typical reaction times at 28° C. for optical purities of 90 percent and above are at least about 2 hours and can range up to about 96 hours for greater conversions and higher optical purities, e.g. optical purities exceeding 95 percent. Reaction times can be reduced significantly by increasing the reaction temperature and/or increasing the amount of enzyme added to the reaction solution. S-enantiomers of formula I can be isolated from the reaction mixture and purified by known methodologies such as extraction, distillation, crystallization, column chromatography, and the like.

As will be apparent to those skilled in the art, the process of the present invention can be carried out using microbial cells containing an enzyme having the ability to catalyze the stereo-selective esterification of compounds of formula I'. When using a microorganism to perform the resolution, the present process is conveniently carried out by adding the cells and the racemic starting material to the desired solvent. Cells may be used in the form of intact cells, dried cells such as lyophilized, spray-dried or heat-dried cells, immobilized cells, or cells treated with organic solvents such as acetone or toluene. Cells may also be used in the form of treated cell material such as ruptured cells or cell extract.

Using the methodology of U.S. Pat. No. 4,105,776, the resolved acid of formula I or its chemical equivalent is used to acylate L-proline having the formula

                                                        VIII forming captopril, i.e. the compound of formula III, in the case where $R_1$ in compound I is hydrogen. Preferably $R_1$ in compound I is an

group, such as

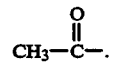

In this case, the thioester formed by the coupling of compound I with compound VIII can be deacylated by conventional means, such as by ammonolysis (e.g., by treatment with alcoholic ammonia or concentrated ammonium hydroxide) or by alkaline hydrolysis (e.g., by treatment with aqueous metal hydroxide). Alternatively, again employing methodology from U.S. Pat. No. 4,105,776, the resolved acid of formula I can be used by removing the acetyl group (by conventional methods) and thereafter dehydrating the so-treated acid to form a thiolactone of the formula

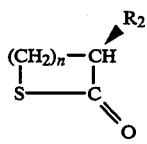
IX

The thiolactone IX can thereafter be used to acylate the L-proline of formula VIII to obtain the desired product.

Similarly, to provide zofenopril, i.e., the compound of formula IV, the resolved acid of formula I or its chemical equivalent where $R_1$ is

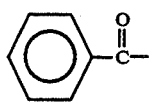

is used to acylate a compound of the formula

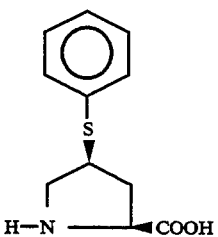
X as described in U.S. Pat. No. 4,316,906. Alternatively, using the methodology of U.S. Pat. No. 4,316,906, the compound of formula I where $R_1$ is

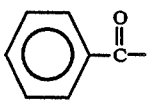

can be coupled with a compound of the formula

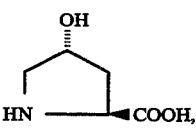
XI or esters or protected forms thereof, to provide a compound of the formula

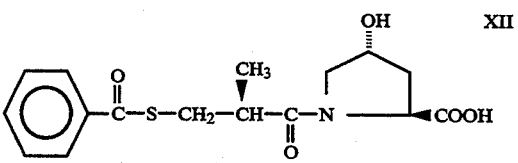
XII which can thereafter be treated with a compound of the formula

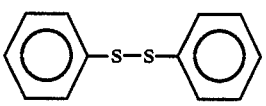
XIII or

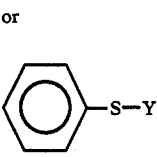
XIV where Y is an activating group such as succinimide or phthalamido or a halide such as Cl or Br to provide the product of formula IV.

The acylation of compounds VIII, X or XI with the resolved acid of formula I can be effected in the presence of a coupling agent like dicyclohexylcarbodiimide or the like, or the acid can be activated by formation of its mixed anhydride, symmetrical anhydride, acid chloride, acid ester or use of Woodward reagent K, N-ethoxy-carbonyl-2-ethoxy-1,2-dihydroquinoline or the like. For a review of the methods for acylation, see *Methoden der Organischen Chemie* (Houben-Weyl), Vol. XV, part II, page 1 et seq. (1974).

The present invention will now be described by the following examples, however, it should be understood that the invention is not meant to be limited by the details therein.

Example 1

Racemic 3-benzoylthio-2-methylpropanoic acid (SQ 32,979; 6.726 g; 0.03 mol; 22.42 mg/ml) and methanol (3.845 g, 0.12 mol) were dissolved in and diluted with toluene to 300 ml. Crude Amano lipase P-30 (12 g; 40 mg/ml; *Pseudomonas fluorescens*) and deionized water (300 μl) were added and the reaction mixture was incubated at 28° C. on a shaker at 280 RPM. The esterification was monitored by capillary gas chromatography (GC) with a flame ionization detector (FID) to determine reaction yields. At 198 hours 2.475 g of the remaining unreacted substrate, that is, S(−)3-benzoylthio-2-methylpropanoic acid (SQ 25,680), had an optical purity of 97.1% with a reaction yield of 37% (results shown in Table 1). In this and all following examples, the enantiomeric composition of the unreacted 3-benzoylthio-2-methylpropanoic acid fraction was determined by capillary gas chromatography following derivatization with thionyl chloride and esterification of the resulting acid chloride with (S)-(+)-2-octanol to form diastereomeric esters which can be separated by capillary GC.

Examples 2–4

Following the procedure of Example 1, additional resolutions were carried out with methanol, benzyl alcohol and 1-octanol. The results are summarized in Table 2.

TABLE 1

| Enzymatic Resolution of SQ 25,680 | | | | | |
|---|---|---|---|---|---|
| Reaction Time (hr) | Conversion (%) | Reaction Yield (%) | Optical Purity (%) | e.e. (%) | Enantiomeric Ratio E |
| 0 | 0 | 100 | 50.0 | 0.0 | |
| 136 | 57 | 43 | 92.3 | 84.6 | 12 |
| 159 | 58 | 42 | 95.0 | 90.0 | 15 |
| 166 | 59 | 41 | 95.5 | 91.0 | 14 |

TABLE 1-continued
Enzymatic Resolution of SQ 25,680

| Reaction Time (hr) | Conversion (%) | Reaction Yield (%) | Optical Purity (%) | e.e. (%) | Enantiomeric Ratio E |
|---|---|---|---|---|---|
| 198 | 63 | 37 | 97.1 | 94.2 | 12 |

Reaction system: 0.1M SQ 32,979 (22.42 mg/ml), 0.4M methanol in 300-ml toluene; 300 uL (0.1% v/v) deionized H₂O added to reaction mixture.
Enzyme: 12.0 g (40 mg/ml) Amano lipase P-30 (from *Pseudomonas fluorescens*)
Conditions: 28° C., 280 rpm.

TABLE 2

| Ex. No. | Alcohol | Reaction Time (hr) | Conversion (%) | Reaction Yield (%) | Optical Purity (%) | e.e. (%) | Enantiomeric Ratio E |
|---|---|---|---|---|---|---|---|
| 2 | Methanol | 0 | 0.0 | 100.0 | 50.0 | 0.0 | |
| | | 16 | 5.8 | 94.2 | | | |
| | | 40 | 33.5 | 66.5 | 63.8 | 27.6 | 4.5 |
| | | 112 | 50.3 | 49.7 | 91.7 | 83.4 | 27.0 |
| | | 136 | 55.1 | 44.9 | 95.4 | 90.8 | 20.7 |
| | | 162 | 63.0 | 37.0 | 97.3 | 94.6 | 11.9 |
| | | 280 | 76.5 | 23.5 | 97.7 | 95.4 | 5.8 |
| | | 328 | 81.1 | 18.9 | 97.5 | 95.0 | 4.7 |
| 3 | Benzyl alcohol | 0 | 0.0 | 100.0 | 50.0 | 0.0 | |
| | | 16 | 10.9 | 89.1 | N.A. | | |
| | | 40 | 26.2 | 73.8 | 56.0 | 12.0 | 2.3 |
| | | 112 | 39.1 | 60.9 | 71.9 | 43.8 | 8.1 |
| | | 162 | 53.3 | 46.7 | 84.7 | 69.4 | 8.3 |
| | | 280 | 66.9 | 33.1 | 96.0 | 92.0 | 8.0 |
| | | 328 | 69.9 | 30.1 | 96.2 | 92.4 | 6.9 |
| 4 | 1-Octanol | 0 | 0.0 | 100.0 | 50.0 | 0.0 | |
| | | 16 | 9.8 | 90.2 | N.A. | | |
| | | 40 | 24.8 | 75.2 | 54.0 | 8.0 | 1.8 |
| | | 112 | 34.0 | 66.0 | 68.0 | 36.0 | 7.9 |
| | | 162 | 48.7 | 51.3 | 78.5 | 57.0 | 7.0 |
| | | 280 | 68.0 | 32.0 | 95.1 | 90.2 | 7.0 |
| | | 328 | 70.6 | 29.4 | 96.8 | 93.6 | 7.0 |

Reaction system: 0.1M SQ 32,979 (22.42 mg/ml), 0.4M alcohol (indicated above) in 25 ml toluene; 25 μL (0.1% v/v) deionized H₂O added to reaction mixture.
Enzyme: 1.0 g (40 mg/ml) Amano lipase P-30 (from *Pseudomonas fluorescens*).
Conditions: 28° C., 280 rpm.

What is claimed is:

1. A process for the preparation of an S-enantiomeric product of the formula

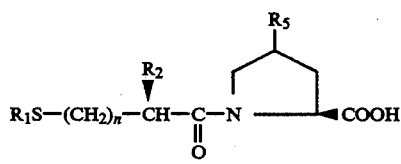

or a pharmaceutically acceptable salt thereof, where $R_1$ is hydrogen or

$R_2$ and $R_3$ are each independently alkyl, cycloalkyl, aralkyl, aryl;
$R_5$ is hydrogen

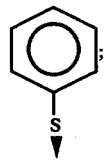

and, n is 1 or 2; which process comprises reacting a racemic mixture of a compound having the formula

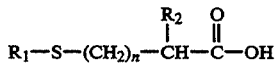    I' with a compound of the formula $R_4$—OH,    VIII where $R_4$ is alkyl, cycloalkyl, aryl or arylalkyl, using Lipase P30 or a microorganism capable of providing Lipase P30, and in a mixed solvent comprising an organic solvent and from about 0.2 to about 100 mg of water per milliliter of solvent, which catalyzes the stereoselective esterification of compounds of formula I' to provide a solution containing R-enantiomeric esters and S-enantiomeric unreacted acids of the formula

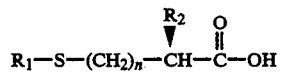    I separating and recovering the S-enantiomeric acid of formula I from said solution; and thereafter A) coupling an S-enantiomeric acid of formula I where $R_1$ is

with a compound of the formula

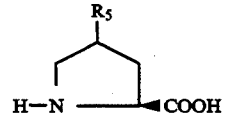

and optionally hydrolyzing the

moiety; or

B) coupling an S-enantiomeric acid of formula I where $R_1$ is hydrogen with a compound of the formula

C) removing the acetyl group from an S-enantiomeric acid of the formula

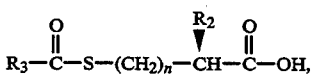

dehydrating the so-treated acid to form a thiolactone of the formula

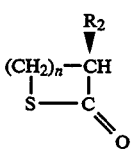

and acylating a compound of the formula

with said thiolactone; or

D) coupling an S-enantiomeric acid of the formula

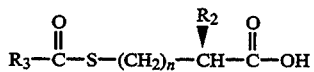

with a compound of the formula

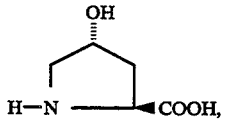

including esters thereof, and treating the so-formed intermediate with a sulfide or disulfide.

2. The process of claim 1 wherein $R_4$—OH is selected from the group consisting of methanol, benzyl alcohol and 1-octanol.

3. The process of claim 1 wherein said S-enantomeric product is

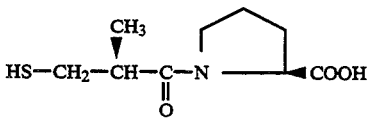

or a pharmaceutically acceptable salt thereof.

4. The process of claim 1 wherein said S-enantiomeric product is

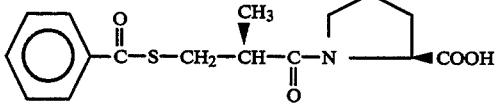

or a pharmaceutically acceptable salt thereof.

* * * * *